(12) United States Patent
Soini et al.

(10) Patent No.: US 6,204,068 B1
(45) Date of Patent: Mar. 20, 2001

(54) BIOSPECIFIC ASSAY METHOD

(75) Inventors: Erkki Soini, Krypingintie 20, FIN-21610 Kirjala (FI); Pekka Hänninen, Turku (FI)

(73) Assignee: Erkki Soini, Kirjala (FI)

( * ) Notice: Subject to any disclaimer, the term of this patent is extended or adjusted under 35 U.S.C. 154(b) by 0 days.

(21) Appl. No.: 08/836,001
(22) PCT Filed: Jan. 3, 1996
(86) PCT No.: PCT/FI96/00005
  § 371 Date: May 13, 1997
  § 102(e) Date: May 13, 1997
(87) PCT Pub. No.: WO96/27798
  PCT Pub. Date: Sep. 12, 1996

(30) Foreign Application Priority Data

Mar. 7, 1995 (FI) .......................................... 951040

(51) Int. Cl.⁷ .......................... G01N 21/64; G01N 33/53; G01N 33/72; G01N 33/537
(52) U.S. Cl. ................. 436/518; 436/7.1; 436/6; 436/7; 436/172; 436/501; 436/164; 436/524; 436/519; 436/7.92; 436/532; 436/533; 436/800; 436/807; 436/81; 436/534; 436/520; 422/82.05; 422/82.09; 435/7; 352/432; 352/433; 352/318; 352/335
(58) Field of Search ........................... 436/7.1, 6, 7, 172, 436/501, 518, 164, 524, 519, 520, 527, 52, 792, 532, 533, 534, 63, 537, 800, 807, 81; 356/432, 433, 318, 434, 436, 437, 440, 491, 442, 335–342, 345, 346; 250/458.1, 461.1, 462.1, 423 P, 459.1; 365/127, 106; 422/82.05, 82.09, 81

(56) References Cited

U.S. PATENT DOCUMENTS

| 4,421,860 | * | 12/1983 | Elings et al. ........................... 436/518 |
| 5,028,545 | * | 7/1991 | Soini ...................................... 436/501 |
| 5,034,613 | * | 7/1991 | Denk et al. ......................... 250/458.1 |
| 5,523,573 | * | 6/1996 | Hanninen et al. ................. 250/459.1 |
| 5,600,444 | * | 2/1997 | Tong ...................................... 356/432 |
| 5,674,698 | * | 10/1997 | Zarling et al. ....................... 435/7.92 |
| 5,736,410 | * | 4/1998 | Zarling et al. ........................ 436/172 |

FOREIGN PATENT DOCUMENTS

| 723146A1 | * | 9/1993 | (EP) ................................ G01N/21/64 |
| 0 269 362 A2 | * | 6/1988 | (WO) ............................. G01N/33/72 |
| WO 94/07142 | * | 3/1994 | (WO) ............................. G01N/33/58 |
| WO 94/16313 | * | 7/1994 | (WO) ............................. G01N/21/64 |
| WO 94/23299 | * | 10/1994 | (WO) ........................... G01N/33/558 |

\* cited by examiner

Primary Examiner—Long V. Le
Assistant Examiner—Lisa V. Cook
(74) Attorney, Agent, or Firm—James C. Lydon

(57) ABSTRACT

This invention is thus related to a biospecific multiparameter assay employing single molecule detection. In particular, this invention is related to a new method for determination of several different biomolecules simultaneously in the same reaction solution. The method uses a fluorescent label for labelling biospecific primary probes and a combination of other labels, bound to secondary probes. Complexes are formed comprising primary probes, analyte molecules and secondary probes in the biospecific reaction. These single molecule complexes are counted selectively while discriminating the signals from other fluorescent molecules using confocal fluorometry or two-photon excitation fluorometry including an auto- and cross-correlator for the signals obtained from said fluorescent labels.

6 Claims, 1 Drawing Sheet

BIOSPECIFIC ASSAY METHOD

FIELD OF THE INVENTION

This invention relates to a biospecific multiparameter assay method for simultaneous measurement of multiple analytes from one single sample.

The invention relates further to a counting method for single fluorescent molecules or their complexes.

BACKGROUND OF INVENTION

Immunoassay is an established biospecific assay method and is widely used in routine diagnostics and research laboratories. Another group of biospecific assays is DNA and RNA hybridization assays, although they are still under development. Two biospecific probes, a primary probe and a secondary probe (i.e., an antibody, DNA or RNA probe) are usually used in biospecific assays. They are both bound to the specific determinants of the analyte molecules and form a complex of three molecules (sandwich structure). Normally, one of these two reagents is labelled. Nowadays, the most commonly used labels are radioisotopes, enzymes, luminescent and fluorescent labels. Later in the text, the label used in a biospecific reaction will be referred to as a photoluminescent label, which denotes labels that generate or catalyse fluorescence, phosphorescence, chemiluminescence or bioluminescence.

There is a constantly increasing need for multiparameter analytics within routine diagnostics. Unfortunately, the existing techniques do not allow the use of more than two or three labels to be measured simultaneously because the spectrometric signals from different labels can not be sufficiently separated. The emission spectra of the photoluminescent labels overlap significantly and as a consequence they provide inadequate separation of different analytes over a required concentration range.

The purpose of this invention is to present a better method for multiparameter biospecific assays. The method according to this invention is based on methods that are generally known within the fields of immunology and DNA hybridization. Normally, they are performed as follows. The method uses two biospecific probes that recognize the analyte molecule k. In this text, these probes are referred to as the primary probe Ab(k,1) and the secondary probe Ab(k,2). When the secondary probe is labelled, for example, with a photoluminescent label F, it is denoted with the symbol $Ab^F(k,2)$. In the reaction solution, there is an excess of primary and secondary probes compared to the number of analyte molecules $M_k$. When the analyte molecule, which is either a polypeptide or a macromolecule, has separate epitopes i.e. molecule structures that bind specifically to the probes, they form a complex $Ab(k,1)+M_k+Ab^F(k,2)$. In principle, the amount of complex formed is directly proportional to the amount of the analyte, and the excess of primary and secondary probes remain in the solution. The complexes are separated from the free probes using a commonly known technique, for example, in which the primary probe is bound to a solid carrier and the free probes are washed away from the sample. Finally, the signal of bound label F in the complexes is measured in a traditional way which depends on the label chosen. The intensity of the signal obtained is directly proportional to the amount of label in the solution, and the response of the system is linear.

If the analyte to be measured is a small molecule without two or more epitopes which specifically bind to the probes, one can use a secondary probe that reacts specifically with the complex formed by the analyte and the primary probe (C. H. Self & al., Clin Chem 40 (1994) 2035–2041).

Principles of a multiparameter biospecific assay have been published earlier. It has been common practice to use multiple labels to tag biospecific reagents and to perform the separation of the signals on the basis of their different emission spectra. In most cases, however, the known multiparameter methods are based on the use of a solid support where the biospecific reagents can be immobilized at separate and optically distinguishable areas, or they are based on the use of artificial microparticles as a solid support. Some of the methods are reviewed below:

1. A method, in which various biospecific probes are attached to a matrix, which is formed by small areas on a planar solid support, is described in the patent PCT WO 84/01031. In this method, after the reaction and the wash, the signals from the photoluminescent labels in each area are measured separately, for example, using a laser scanning microscope.

2. A method, in which the identification of the analyte category is based on the color of the microparticles, which are used as a solid support and which is achieved by optically measuring the light absorption of the particle to be analyzed (J. G. Streefkerk & al., Protides Biol. Fluids 24 (1976) 811–814 and U.S. Pat. No. 5,162,863).

3. A method, in which the identification of the analyte category is performed by optically measuring the absorption of the dye inside the particle, the refractive index or the size of the particle to be analyzed (U.S. Pat. No. 5,162,863).

4. A method, in which the identification of the analyte category is based on the use of different particle sizes and in which the identification is performed by optically measuring the diameter of the particle to be analyzed (T. M. McHugh & al., Journal of Immunological Methods 95 (1986) 57–61).

5. A method, in which the microparticles are identified by means of fluorescent dyes that are mixed or impregnated within the particles, and the biospecific signal is measured from the fluorescence intensity of another fluorescent dye, such as FITC (EP 126450, GOIN 33/58).

6. A method, in which a dye emitting short decay time fluorescence (decay time a few nanoseconds) is used for the identification of microparticles, and a dye emitting long decay time fluorescence (decay time from 10 microseconds to 2 milliseconds) is used for measuring the analyte concentrations, and in which a time resolved fluorometer is used for the discrimination of the short and long life time fluorescence (U.S. Pat. No. 5,028,545).

7. A method, in which a dye emitting short decay time fluorescence (decay time a few nanoseconds) is used for the identification of the microparticles, and a molecule which generates chemiluminescence or bioluminescence (decay time several seconds) is used to measure the analyte concentrations, and in which the fluorescence and luminescent signal can effectively be separated from the fluorescence because they are excited and they emit light at different times (FI-patent 89837).

8. A method, in which a dye emitting short decay time fluorescence (decay time a few nanoseconds) is used for the identification of the microparticles and a dye emitting phosphorescence, (decay time from 10 microseconds to 2 milliseconds) is used to measure the analyte concentrations, and in which a time resolved fluorometer is used for the discrimination between the short decay time fluorescence and the long decay time phosphorescence (FI-patent 90695).

9. A method, in which dyes emitting long decay time fluorescence, such as fluorescent chelates of lanthanide ions Tb, Dy, Eu and Sm, are used for the identification of the microparticles and for measurement of the biospecific signal (FI-application 931198).

A common problem in many multiparameter assays mentioned above is that the signal of the photoluminescent label, which indicates the analyte category, and the signal from the photoluminescent label, which measures the concentration of the biospecific probe, interfere with each other. This is a problem that significantly restricts the dynamic range of the measurement of the analyte concentration. It is essential for the sensitivity of the method of this invention, as well as for the sensitivity of the multiparameter assays mentioned above and previously known, that the signal from the indicator used for the identification of the analyte does not interfere with the signal from the photoluminescent label used for the measurement of the biospecific reaction. This interference may become particularly significant when measuring low analyte concentrations and when a wide dynamic range is required for the measurement of the biospecific signal. In methods 6, 7, and 8 referred to above, interference is eliminated by choosing such photoluminescent labels for the measurement of the biospecific reaction and identification labels which have substantially different emission decay times. In methods 1, 2, 3 and 4 the analyte is identified using an alternative method rather than using a photoluminescent label. In methods 5 and 9, the identification method of the analyte essentially restricts the dynamic range of the measurement.

Another problem with methods 6, 7, 8 and 9 mentioned above is the long measurement time, caused by the long decay time (T½=1 millisecond) of the fluorescent and phosphorescent labels. This is due to the saturation of the excited states of the labels, which restricts the intensity of the exciting light to such a low level that a measurement time of up to one second is needed for each microparticle.

Likewise, the measurement of the signals from labels that are based on chemiluminescence, bioluminescence and electroluminescence, also take at least one second.

SUMMARY OF THE INVENTION

In one aspect, the invention relates to a biospecific multiparameter assay method for simultaneously measurement of multiple analytes $M_k$ (k=1, 2, ..., k) in the same reaction solution, said method comprising the steps of allowing each sample molecule $M_k$ to react with at least two biospecific probes Ab(j) (j=1,2) labelled with fluorescent labels, to give a complex Ab(k,1)+$M_k$+Ab(k,2), stopping the reaction by adding a diluent, focusing a laser beam and photon detectors tuned to the excitation and emission wavelengths, respectively, on the diluted solution, registering the fluorescent signals and their time domains in the form of single photons from single molecules moving through a focal point. The method is characterized in that the first biospecific probe is labelled with a combination of fluorescent labels $D_1, D_2, D_3, \ldots D_k$, denoted as $D_k$, and the second probe is labelled with a fluorescent label F, and the signals from the complexes $Ab^{Dk}$(k,1)+$M_k$+$Ab^F$(k,2) are separated from the background signals and from the signals of other molecules by applying auto-correlation in time domain and cross-correlation with regard to signals obtained from different labels, and the correlating signals are classified according to $D_k$ in order to determine the number of analyte molecules $M_k$ and their concentration in the sample, and that the excitation and detection of the labels $D_k$ and F is performed with a confocal optical system, or the excitation of the labels $D_k$ and F is performed by two-photon excitation.

In another aspect, the invention relates to a counting method for single fluorescent molecules or their complexes comprising the steps of:

focusing a laser beam and a photon detector to a diffraction limited volume containing the labelled fluorescent molecule, registering single photon signals and their time domains from single molecules moving through a focal volume around the focal point. The method is characterized in that the excitation of the fluorescence of the molecules or their complexes is performed by two-photon excitation and the signals from the fluorescence are separated from background signals by means of auto-correlation in the time domain.

DETAILED DESCRIPTION OF THE INVENTION

Figure 1:
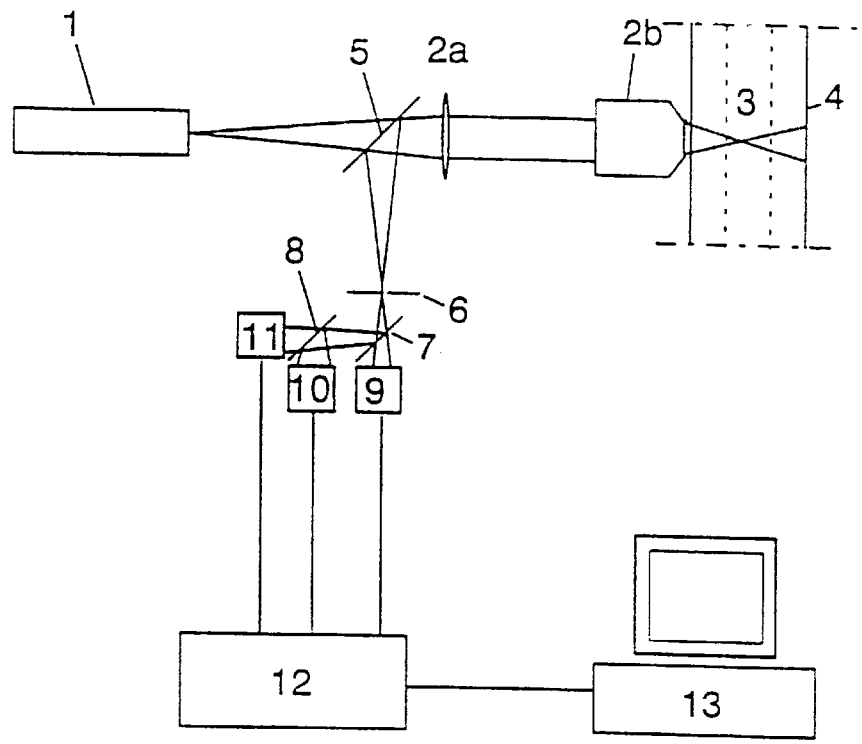
FIG. 1 is a functional diagram of the measuring system needed for the method of this invention.

This invention is thus related to a biospecific multiparameter assay using fluorescent labels for labelling the biospecific probes based on the use of molecule counting in which the number of molecules bound by the biospecific reactant are determined. Molecule counting means that the method employs a sensitive single photon counting system which is able to register fluorescent signals from individual fluorescent complexes of biospecific molecules in the solution.

Counting of single molecules with a confocal fluorometer within a very small measurement volume, limited by the diffraction of light, is known in the literature (A. Castro & al., Anal Chem 65 (1993) 849–852; S. Nie & al., Science 266 (1994) 1018–1021, EP 0381694, WO 90/14589).

This invention involves a new method for multiparameter biospecific assay employing the methodology of single molecule detection. In particular, this invention is related to a new method for determination of several different biomolecules simultaneously in the same reaction solution. The method uses a fluorescent label for labelling biospecific primary probes and a combination of other labels bound to secondary probes. Complexes are formed comprising primary probes, analyte molecules and secondary probes in the biospecific reaction. These single molecule complexes are selectively counted: the signals from other fluorescent molecules are discriminated using confocal fluorometry or two photon excitation fluorometry including auto- and cross-correlation of the signals obtained from said fluorescent labels.

In the method used by this invention, the complexes are between the complexes and the free fluorescent labels $Ab^F$(k,2) with molecule counting, this method uses another fluorescent label D in addition to the fluorescent label F. The label D is bound to the primary probe Ab(k,1). Thus, the structure of the molecular complexes to be counted is $Ab^{Dk}$(k,1)+$M_k$+$Ab^F$(k,2). In the method of this invention, the selectivity of molecule counting is based on confocal fluorometry, or on two-photon-excitation fluorometry, and on auto-correlation and cross-correlation in the time domain of the signals from the fluorescent labels F and D. This will be explained more in detail later. In the method of this invention, the multiparametricity, i.e. the measurement of many analytes simultaneously from the same reaction solution, is based on the method in which a combination of fluorescent labels $D_1$, $D_2$, $D_3$, ... $D_k$, is used as primary labels, denoted as $D_k$, for the purpose of identification of the analyte. The emissions of the labels $D_1$, $D_2$, $D_3$, ... $D_k$ appear at different wavelengths that can be separated spectrally from each other. With the correlation calculation approach mentioned above, the index k from the combination of labels $D_k$, functions as an additional parameter and expresses the name (later category) of the analyte $M_k$.

The method of this invention includes the following steps:

the analyte $M_k$ and the probes $Ab^{Dk}(k,1)$ and $Ab^F(k,2)$ are added to a suitable reaction solution (k=1, 2, 3, ..., k), the reaction is stopped by adding a diluent, the diluted sample is fed through a thin flow cell, the laser beam and the photon detectors, of which the latter are tuned to the emission wave lengths of the labels F and $D_k$, are focused to the moving sample with an optical system, the single photon fluorescence signals from single molecules are registered together with the arrival time of the signal, the signals from the complexes $Ab^{Dk}(k,1)+M_k+Ab^F(k,2)$, are separated from the noise signals and the signals from other molecules by applying auto-correlation and cross-correlation in the time domain to the single photon counts, the signals above are classified according to the index k, and thus numerical results that correspond to the number $M_k$ of the analyte molecules and their concentrations are obtained.

The Advantages of the Invention Compared to Known Methodology

The strength of the biospecific reaction is that the analyte concentration is measured in this method as the number of molecular complexes produced by the biospecific reaction. The signal is obtained from each individual molecular complex separately. Since in molecule counting the signals are characteristically 0 or 1, a very narrow dynamic range is sufficient for measuring the fluorescence signals F and $D_k$. Thus, conventional fluorescent labels can be used to identify the category and to measure the biospecific signal without any harm from the interference caused by the overlapping spectra of different fluorescent labels. This means that the identification signal does not interfere with the biospecific signal, although both have a short decay time and normal spectrometric methods are used to discriminate between the signals.

In the method of this invention, conventional organic fluorescent dyes can be used as fluorescent labels F for the biospecific reagents. The advantages of these dyes are their high absorption of the exciting light and the high quantum efficiency of the fluorescence.

Since fluorescent labels with an emission decay time of some nanoseconds are used in the method of this invention, the intensity of the exciting light may be up to $10^6$ times higher, than the excitation intensity of the long decay time fluorescent labels—A much stronger signal can be derived from labels with a short decay time and, correspondingly, it can be measured much faster. This has the advantage that the time needed for detecting one molecule is very short, for example, 100 microseconds, and many molecules can be measured within the time that is available for one assay, resulting in higher accuracy and precision.

The Realization of the Invention with the Confocal Principle

FIG. 1 is a functional diagram of the measuring system needed for the method of this invention. It is realized with the confocal principle. The diagram shows an example where it has been assumed that two fluorescent labels, d1 and d2, whose combination is marked with the symbol $D_k$, are used for the identification of the analyte. The function of the device is as follows. The laser (1) used for the excitation of fluorescence is focused to the cuvette (4), containing the sample (3) through a lens (2a) and an objective lens (2b). The fluorescence signal from the sample is directed through a pinhole (6) and dichroic mirrors (7) and (8) to detectors of (9), (10) and (11), which are tuned to emission wavelengths of the label F, d1 and d2 respectively. The detectors (9), (10) and (11) are connected to a signal processor (12). The signal processor handles the correlation calculations and the results are processed in the computer (13), which also controls the hardware. The labels F and $D_k$ can also be excited with different lasers, if their excitation wavelengths are different, or if better results is achieved by using two lasers. In this case, both lasers are focused to the same or adjacent points of the moving sample.

The principle of the confocal set-up is described below with reference to FIG. 1. Firstly, the imaging of a point-like source of light (1) to the focal plane (3) of the objective lens (2b) is described. Due to diffraction, a point-like source of light forms an intensity distribution, which is characteristic to the optical system, in the focal plane. The intensity distribution is called the point spread function, which is determined in three dimensions. A normalized point spread function defines the probability S1 of how photons, radiated from a point-like light source, are distributed on the focal area (3); that is, the probability that the photons are absorbed to different parts of the sample volume.

A corresponding point spread function S2 can also be determined for the spatial distribution of the photons emitted from the focal point that reach the pinhole (9) in front of the detectors. The value of this normalised function in the vicinity of the focal point defines the probability of the photons emitted from different points hitting the pinhole (6).

In the confocal optical system that has been applied to the method and the device of this invention, the light source (1) and the pinhole (6) are focused to the same focal point (3). The probability that a photon radiated from a point-like light source (1) causes a fluorescence emission in the sample, and that the emitted photon hits the pinhole (6), is described in a confocal system by the normalized product S1*S2 of the illumination and detection intensity distributions. The probability distribution thus derived, is three dimensional and is clearly more restricted than the one produced by conventional optics, especially in the axial direction. The fluid volume to be measured in a confocal system is considerably smaller than the one in a conventional optical system. When using an objective lens with a large numerical aperture (N.A.=1.4) and a confocal system, the active fluid volume is reduced to under a tenth of what is required in a conventional optical system. The fluid volume under observation, is clearly larger axially than laterally, and it is proportional to the square of the numerical aperture.

The active fluid volume can be reduced further by a confocal principle already documented in the literature (Eur. patent appl. 91121368.4), in which the numerical aperture of the system is increased with two objective lenses positioned opposite each other for the confocal observation of the sample. In this system, illumination and detection take place simultaneously and coherently through both objective lenses and the fluid volume that is under observation is further reduced to at least half, compared with a conventional confocal microscope with one objective.

Additionally, the sensitivity of detection is improved because of the higher numerical aperture.

If it is not possible to use an objective with a high numerical aperture in a confocal system, it is possible to reduce the volume under observation axially by using, for example, two confocal objectives mounted at a 90 degree angle to each other (E. Steltzer & al., Opt. Commun. 111 (1994) 536–547). This method does not increase the numerical aperture of the system, as in the method described above, but it is practical in reducing background signals and especially backscattering.

In spite of the confocal measuring system, the background signal caused by scattering and autofluorescence reduce the sensitivity of molecule counting. It is known, though, that when measuring the signal of fluorescent labels, background signals may be reduced by using auto-correlation of signals from stochastic Poisson distributed photons from the detector, in addition to good spectral discrimination. (PCT WO 94/16313; S. A. Soper & al., Anal Chem 63 (1991) 432–437; M. Eigen & al., Proc Nat Acad Sci USA 91 (1994) 5740–5747).

In addition to auto-correlation documented in the literature, the discrimination of the signals derived from single molecules is improved by cross-correlation of the signals F and $D_k$ in the method according to this invention. In this invention, cross-correlation is applied to distinguish the complexes $Ab^{Dk}(k,1)+M_k+Ab^F(k,2)$ from free, labelled compounds. To meet the cross-correlation condition, the auto-correlation conditions for each label of the complex also need to be met within the measurement time window. For example, in a complex with one F and one D label, the probability of reaching the cross-correlation condition is the product of the probabilities of meeting the conditions of the auto-correlation function for F and D. The cross and auto-correlations of the pulse train are calculated with the signal processor or with the combinatory logic of the device (12) shown in FIG. 1.

Figure 2:
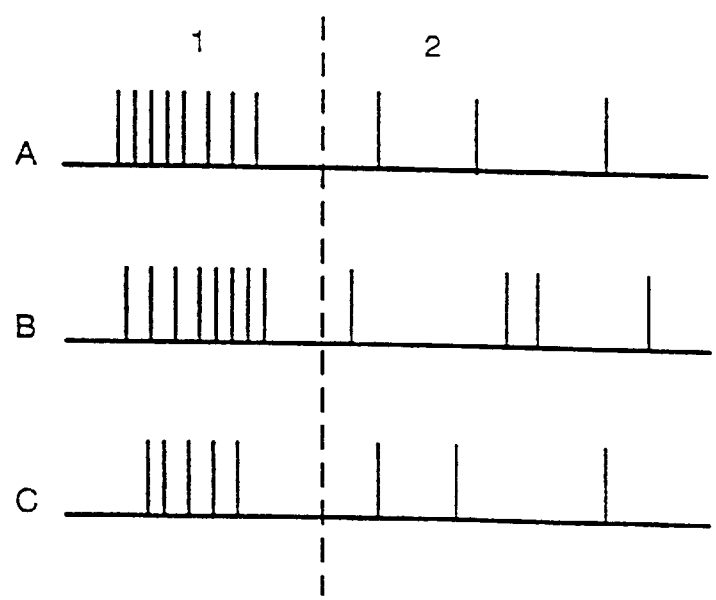
FIG. 2 presents an example of signals derived from the detector.

The signals from the detectors (9), (10) and (11) in FIG. 1 are characteristically single photon signals, which are transformed to binary digital signals with a duration, for example, for 10 nanoseconds. FIG. 2 presents an example of pulses derived from the detectors (9), (10) and (11) (FIG. 1) in the time scales (A), (B) and (C). A molecule stays for the time $t_m$ under the excitation of the laser beam within the volume defined by the point spread function of the confocal optics. In practice, the time $t_m$ depends on the speed of the flow inside the cuvette (4, FIG. 1), and is typically 100 microseconds. The intensity of the laser beam, used for the excitation of label F, is so high at the focal point (3) that it can nearly saturate the excited states. Because the decay time of the fluorescent labels F is only about 1–10 nanoseconds, within the time interval $t_m=100$ microseconds, they are excited and relaxed $10^4$ times under the influence of a powerful laser beam. The number of photons observed by the detector, depends on the quantum efficiency of the label F, the collection efficiency and the losses due to the optics (2a, 2b, 4) and the quantum efficiency of the photon detector (9). In practice, a detection efficiency of $10^{-3}$ can be obtained when using photomultiplier tubes and $10^{-2}$ when using avalanche photon counters with 80% quantum efficiency (EG&G Optoelectronics, Canada, type SPCM-141-AQ). Within the exposure time $t_m$ of the laser beam, the detector (9) can detect a minimum of 10 photons from the fluorescence emission which comes from one molecule flowing through the active volume. The photons appear as stochastic photon bursts within the time interval of $t_m$ (section 1, FIG. 2). In addition to these bursts, many other stochastic signals may also be detected (section 2, FIG. 2). They originate from the background fluorescence, other molecules in the sample, scattering and thermal noise. The majority of the stochastic signals can be eliminated with auto-correlation by choosing proper auto-correlation parameters. Similarly, the signals caused by several complexes together or by aggregated molecules, can be eliminated by the proper choice of auto-correlation parameters.

The avalanche diode photon counter may generate spontaneous after-pulsing with the probability of $10^{-3}$. Avalanche photon counters, as well as photomultiplier tubes, suffer from thermal noise which appears as stochastic counts. The afterpulsing and the noise can be eliminated with the following alternative methods. Auto-correlating the signals from avalanche photon counters with a threshold of 3 counts or higher eliminates the background caused by after-pulsing, but this is made at the cost of detection efficiency. By dividing the emission beam into two parts with a 50%/50% beam splitter for two separate photon counters and using a cross-correlator, it is possible to discriminate the after-pulses and thermal noise. The increased optical losses can be compensated with increased laser power.

The device (12) in FIG. 1 performing the correlation analysis for single photon bursts can be an electronic logic circuit, which gives an output signal if a pre-set number of single photon counts from each detector arrives within a pre-set period of time. The circuit may also perform more complex correlation functions or the circuit may be replaced by special computing software which is loaded into a dedicated signal processor or onto a conventional computer.

Throughout, it has been assumed that, depending on the speed of the flow, a molecule stays under the excitation of the laser beam for 100 microseconds. Since molecules arrive randomly to the laser beam, and because a combination of two particles or more is not allowed, the counting frequency of the molecules can at most be 1,000 molecules/s. If, for example, 10,000 molecules of each kind are to be counted and if there are 10 different kinds, then altogether it would take for 100s to measure one sample.

The fluorescence signals of the chromophores $D_k$ appear as similar bursts (B and C in FIG. 2) as that of F, and they are detected, as described above, with photon detectors (10 and 11, FIG. 1) that are tuned onto the emission wavelength of the chromophores $D_k$. In addition to auto-correlation, the cross-correlation of the signal F and the signals $D_1$ and $D_2$ is applied to the signal analysis. This means that the signals A, B and C (FIG. 2) from detectors (5), (6) and (7) (FIG. 1), respectively, are correlated. In this way, a significant portion of the molecule complexes $Ab^{Dk}(k,1)+M_k+Ab^F(k,2)$ flowing through, can be detected; and simultaneously, the level of background signals from other sources can be minimized. The sensitivity of the system is defined by the relation between the rate of signals selected with the correlation method and those that arise from the random background and from the formation of non-specific complexes. It is obvious that stricter correlation conditions decrease the rate of accepted pulses from the molecules, but the rate of erroneous counts decreases even more rapidly, and thus the signal-to-noise-ratio is improved. In this case, in order to achieve the required statistical precision, a larger sample volume is therefore needed. Similarly, correlation conditions must be optimized separately for each application.

EXAMPLE

An example calculation of applying auto-correlation and cross-correlation in a hypothetical measuring situation, is shown below. It has been assumed that in the active volume there is one F and one D, their quantum efficiency is 100%, the time window is 100 microseconds and the thermal background of the detector is $10^4$ pulses/s. The optical and electronic detection efficiency of the system for single photons is $10^{-3}$, the lifetime of the excited states of the label is 5 ns and the excitation rate of the excited states of the label caused by that is $2*10^7$ /s, and the limit of acceptance of auto-correlation is 60% of the expectation value 1 (however, to the nearest larger integer a).

TABLE 1

| N(F) | N(d) | S/N | P(det) |
|---|---|---|---|
| 1 | 1 | 5.1 | 0.35 |
| 1 | 2 | 21 | 0.45 |
| 2 | 4 | $2.3\ 10^3$ | 0.69 |
| 3 | 6 | $4.0\ 10^6$ | 0.77 |
| 4 | 8 | $2.1\ 10^9$ | 0.86 |
| 5 | 8 | $1.8\ 10^{12}$ | 0.91 |

$$P_A = 1 - \sum_{k=0}^{k=a-1} \lambda^k e^{-\lambda}/k! \qquad \text{Equation 1}$$

When the point probability $P_k$ (Equation 1) of a Poisson distribution is applied to the measurement conditions described above (1(sign)=2, l(backgr)=1, a=2), the Poisson probability $P_A$(sign) of detection of a single molecule will be 0.865, and the probability $P_A$(backgr) of detection of a background count will be 0.632. After applying the value of the correlation condition a=2 and Equation 2, the probability of detection of a single molecule count will be 0.59, and the probability of detection of a background count will be 0.26. When the signals of both chromophores are cross-correlated, the probability $[P_A(\text{sign})]^2$ of detection of a molecular complex will be 0.35, and the probability $[P_A(\text{backgr})]^2$ of detection of a background count will be 0.07. Thus, it can be concluded that together auto-correlation and cross-correlation improve the signal-to-noise-ratio from 1.4 to 5.0. Increasing the value of the auto-correlation condition a from 2 to 3 improves the signal-to-noise-ratio to a value of 16.7.

If the probe is labelled with more than one label molecule, or if for some other reason more than one pulse (later referred to as a burst) is obtained from the label within a time window, it is possible to reach an enhancement in the signal-to-noise-ratio using auto-correlation, in which case, the enhancement is significantly higher than in the previous example. Signal-to-background-ratios under different measurement conditions, and with different amounts of fluorescent labels F and D, are presented in Table 1. The notations N(F) and N(d) in Table 1 refer to the number of label molecules F and D per complex, respectively; S/N refers to the signal-to-background-ratio after auto-correlation; and P(det) is the detection probability of the signal after auto-correlation.

It can be concluded from the results of Table 1 that the signal-to-background-ratio, which in this case is equal to the dynamic range of molecule counting, is substantially increased when more than one fluorescent label is used in the complexes. It is obvious that in this case, the non-specific reactions and signals are the main limiting factor the dynamic range.

Two-Photon Excitation

In the literature presented above, the fluorescent labels have been single-photon excited, which means that the chromophores of the fluorescent label absorb light at the wavelength of the laser beam. In the method according to this invention, two-photon excitation can replace single-photon excitation and confocal optics, and reduce the background caused by autofluorescence and particularly by scattering. Two-photon excitation can be used when, by focusing an intensive light source, the density of photons per unit volume and per unit time becomes high enough for two photons to be absorbed into the same chromophore. In this case, the absorbed energy is the sum of the energies of the two photons. Already in the 1930's, two-photon excitation of fluorescent materials was theoretically known, and from the 1960's on it has been applied in the fields of spectroscopy and microscopy (M. J. Sepaniak & al. Anal. Chem. 49 (1977)1554–1556, U.S. Pat. No. 5,034,613). According to the concepts of probability, the absorption of a single photon by a chromophore, is an independent event, and the absorption of several photons is a series of single, independent events. The probability of absorption of a single photon can be described as a linear function as long as the energy states that are to be excited are not saturated. The absorption of two photons is a non-linear process of the second kind. In two-photon excitation, the chromophore is excited only when both photons are absorbed almost simultaneously, that is approximately within a femtosecond. The probability of absorption of two photons is equal to the product of probability distributions of absorption of the single photons. The intensity of fluorescence emission, caused by two photons, is thus a quadratic process with respect to the photon density of illumination.

The properties of this invention's optical system have been described above with respect to the response of the system to a point-like light source. A point-like light source forms, due to diffraction, an intensity distribution in the focal plane characteristic of the optical system (point spread function). When normalized, this point spread function is the probability distribution for the photons from the light source to reach the focal area. In two-photon excitation, the probability distribution of excitation equals the normalised product of the intensity distributions of the two photons. The probability distribution thus derived is 3-dimensional, and is clearly more restricted than that for single-photon excitation, especially in the axial direction. Thus in two-photon excitation, only the fluorescence that is formed in the clearly restricted 3-dimensional vicinity of the focal point is excited.

When a chromophore is two-photon excited and the excitation is restricted to the 3-dimensional vicinity of the focal point, then the signal caused by scattering in the vicinity of the focal point and from the optical components, is reduced remarkably if compared to normal excitation. Furthermore, two-photon excitation decreases the background fluorescence outside the focal point, in the surroundings of the sample and in the optics. Since the exciting light beam must be focused onto as small a point as possible, two-photon excitation best suits the observation of small sample volumes and structures, which is also the situation in the method according to this invention.

The previously mentioned advantages of two-photon excitation are based on the fact that visible or near-infrared (NIR) light can, for example, be used for excitation in the ultraviolet or blue region. Similarly, excitation in the visible region can be achieved by NIR light. Because the wavelength of the light source is considerably longer than the emission wavelength of the chromophore, the scattering at a wavelength of the light source and the possible autofluorescence can be effectively attenuated by using low-pass filters (attenuation of at least 10 orders of magnitude) to prevent them from reaching the detector.

In our experiments, we have observed that a very high signal-to-background-ratio and good sensitivity can be reached with two-photon excitation and short-lived fluorescent labels. Suitable fluorescent labels for two-photon excitation are, for example, coumarin, rhodamine derivatives and phycobiliproteins.

It has been observed that two-photon excitations can be observed with continuous-wave laser illumination, but two-photon excitation can best be performed with pulse lasers. During the short pulse, it is possible to achieve a sufficiently high energy density for two-photon excitation, but the average energy is kept low. The short transit time requires a pulsed laser with very high repetition frequency. Today, the laser suitable for this application is the titanium-sapphire femtosecond laser with pulse energy of 10 nJ and with pulse frequency of 76 MHz and with adjustable 700–900 nm wavelength. Less expensive pulsed lasers suitable for this application will likely be available in the near future. An example of this kind of development is the mode-locked 300 MHz pulsed diode laser (Laser Ionics Inc., Orlando, Fla., USA),=825 nm, pulse energy 0,03 ni, pulse width 1–20 ps. Another example is a new, not yet commercially available diode pumped CrLi-Sapphire laser with 80 MHz pulse rate, 30 fs pulse width, 0.5 ni pulse energy and adjustable 820–900 nm wavelength.

In using the method of two-photon excitation with autocorrelation, the cross-correlation of the signal F and the signals $D_k$ can also be applied to the analysis of the fluorescence signals from the molecular complexes $Ab^{Dk}(k,1)+M_k+Ab^F(k,2)$ flowing past the detector. This is analogous to the previously described alternative, based on the confocal optics. In addition to the auto- and cross-correlations, the coincidence condition of the laser pulse and the pulse from the photon detector can also be used to eliminate thermal noise from the photon detector. In this case, thermal noise becomes insignificant. When the correlation and coincidence methods mentioned above are applied to molecule counting, the lowest detectable concentration of molecular complexes is only dependent on the nonspecific reactions of the labelled biospecific reagents. The use of two-photon excitation is advantageous compared to the confocal method because scattering and background noise, especially that caused by proteins and other macromolecules in the sample, is considerably lower. No fluorescence arises at the wavelength of the laser, nor can scattering caused by the laser beam reach the detector, because low-pass filters effectively block the wavelengths lower than that of the laser.

The equipment for two-photon excitation is similar to the one in FIG. 1, but the laser (1) has been replaced with a more suitable laser for two-photon excitation, and the pinhole (6) has been replaced with a larger aperture stop.

EXAMPLE

As an example of how effectively single molecules can be detected with two-photon excitation, we present results of measurements of a coumarin solution. An optical set-up based on two-photon excitation was used in the measurements, and 5 nM, 500 nM and 50 mM coumarin solutions were used as samples. The active fluid volume at the focal point was approximately 0.06 cubic micrometers (femtoliters) and on average it contained 0.16, 16 and 1600 fluorescent molecules, respectively. Count rates of $10^2$, $10^4$ and $10^6$ pulses/second, respectively, were obtained from the coumarin solutions with the above concentrations, while the background of the photon counter was 30 pulses/second. Based on this result, it can be stated that single molecules that move with thermal diffusion through an active volume of 0.06 femtoliters can be detected by using two-photon excitation in the equipment that was used in the experiment.

Identification of the Category

The chromophores $D_k$ are used, for example, for the binary detection of the analyte, so that either one unit mass or none of the chromophores $D_1, D_2, D_3, \ldots D_k$ is tagged to the probe Ab(l). In this case, $D_1$ expresses the first bit of the binary number, $D_2$ expresses the second, $D_3$ expresses the third bit, and so forth. Thus, for example, with three chromophores, (k=3), $2^k=2^3=8$, eight different analytes can be detected. The capacity of the identification method can be increased so that instead of increasing the number k of the chromophores D, and instead of having a binary system one can switch to using a 3, 4 or, in general, an m-based numerical notation system. In that case, the efficiency will be $3^m$, $4^m$ or $k^m$, respectively.

In practice, the number of chromophores is limited by the availability of suitable dyes, and also by their emission wavelengths, which need to be easily separable. In practice, the number of different categories needed is also rather limited, and usually it does not exceed 10 or 20. In this case, the largest values for k and m are 3 and 3, respectively. That is, different concentration levels of three fluorescent chromophores are used, which gives a maximal number of categories $3^3=27$.

Choice of Fluorescent Labels

Irrespective of whether single- or two-photon excitation is used, several compounds with short fluorescence decay times can be used as labels F and D. It is clear that the measuring device needed in this method becomes simpler, if the excitation wavelength for all of the chromophores F and D is the same, and the emission wavelengths differ sufficiently from each other, so that they can easily be separated spectrally. The measuring device becomes simpler, if the chromophores F and D can both be excited with the same laser beam. This means that, for example, each of the chromophores F and D are two-photon excited or, alternatively, F is two-photon excited and the fluorescent dyes of the NIR region are used as chromophores D and they are single-photon excited with the fundamental wavelength of the same laser. However, if chromophores similar to the ones described above are not used, it is necessary to excite them with two separate lasers, which are focused to the same or adjacent points of the moving sample. The excitation at the points, and the emission followed by it, are separated in time.

As an example of the choice of compound F, the derivatives of coumarin and rhodamine are presented here. Their fluorescence can be excited at wavelength region of 350–400 nm.

The potential fluorescent chromophores D should show the following properties. In the method according to this invention: 1) They must have a common fluorescence excitation wavelength, which lies, if possible, on the excitation range of the bioaffinity label F, or at the fundamental wavelength of the laser that is used for the two-photon excitation of F; 2) they must have spectrally separable fluorescence emission bands that are higher than that of F; 3) the decay time of their fluorescence excited states must be short, and lie in the nanosecond range; in addition, it is advantageous for a good function of this invention if 4) they have a large difference between their excitation and emission wavelengths; 5) they have no significant long decay emission component and 6) they are chemically stable and attachable to the biospecific probes. The following commercially available and widely used dyes meet these specifications: Hoechst 33258, rhodamine (TRITC), Texas Red and Quantum Red. Although the excitation maxima of these dyes lie at different wavelengths, they can still be reasonably well excited at a single wavelength in the 300 to 450 nm range. The emission maxima lie at wavelengths of 470, 570, 620 and 670 nm, respectively. The set of dyes mentioned above can be completed with commercially available laser dyes of the NIR region or with their derivatives, for example IR132 or IR144. These compounds usually have a good absorption in a broad ultraviolet range (320–450 nm), besides the main excitation maximum in the red or the NIR region. Their narrow, separate emission bands lie at wavelengths of 825 nm and 905 nm.

A group of compounds suitable for dyes $D_k$ can be found among the following group of tetrapyrrols: porphyrins, chlorines, bacteriochlorines, purpurines, pheophorbides, phtalocyanines and naphthalocyanine. These compounds generally have overlapping absorption bands at a near-UV range (320 nm–450 nm) and narrow separate fluorescence emission bands at the red and the NIR-range (600 nm–800 nm). We have found that tetrapyrrolic dyes show very low susceptibility to two-photon excitation. Therefore the use of tetrapyrrolic dyes are limited to single photon excitation only. These compounds can be produced synthetically or microbiologically (Porphyrins, D. Dolphin, Ed., Elsevier, Amsterdam-N.-Y.-London, 1980, V. 1–3) and they have been used in various analytical applications (D. B. Papkovsky, Appl. Fluor. Technology 3 (1991) 16–23; EP 0127797; EP 0071991; Russian patent SU 1,659,477).

Examples of tetrapyrrolic dyes are: 1) deuteroporphyrine IX, 2) mesoporphyrine IX, 3) proto-porphyrine (IX) dimethyl ester, 4) octaethylporphin, 5) tetraphenylporphin, 6) tetra-(2-metoxy)-phenyl-porphin, 7) chlorine of coproporphyrin dimethyl ester, 8) bacteriochlorine of coproporphyrin dimethyl ester, 9) aluminium phthalocyanine and 10) zinc phthalocyanines.

A group of tetrapyrrols suitable for dyes $D_k$ could consist of the above-mentioned compounds 1, 6 and 10; their emission wavelengths being 623 nm, 656 nm and 689 nm, respectively. These tetrapyrrolic dyes could be supplemented with other known organic fluorescent compounds having the same excitation wavelength and showing an emission band either within the lower or the higher side of the emission range of tetrapyrrolic compounds.

The detection efficiency of single molecule complexes and the sensitivity of the method could be increased if single fluorescent dyes F and D are replaced with dye clusters consisting of the above-mentioned compounds, because their fluorescence emission is more intense than that of a single molecule. Natural or protein structures modified by gene technology could typically form the frame of dye clusters. A simple example of a cluster suitable for replacing label F is Phycoerythrin. Linear chains, branching molecule clusters, or dendrimers can also be synthesized from labels F and D. The cluster can also be small latex microparticles, in which fluorescent dyes have been added to their polymer structures.

It has been explained earlier how fluorescence signals from molecule complexes $Ab^{Dk}(k,1)+M_k+Ab^F(k,2)$ are separated from scattering and background fluorescence by means of auto-correlation and cross-correlation of labels F and D. It has also been explained that the emission spectra of labels D slightly overlap. Thus, 10% of t he emission of label $D_1$ leaks into the emission detector of label $D_2$. This phenomenon impairs the reliability of the classification, The reliability, however, could be improved significantly by using dye clusters which allow a greater number of photons to be registered. Thus, the probability of errors caused by leakage and other interfering sources can be minimized by using auto- and cross-correlation.

Handling of a Sample

Flow cytometric molecule counting can be performed either in a cuvette or in the open air where instead of a flow cuvette, measurement can be performed on a glass slide or on some other support, in a reaction chamber, in a fluid channel or in a separate measuring cuvette. Detection of molecules may be based on the movement of the sample solution, on diffusion of molecules, on mechanical movement of the sample support or optics. A sufficient amount of complex will be identified and counted in order to achieve the required statistical precision for each analyte. The results are cross-referenced to the measurements of standard samples, and the final results will then be calculated.

This invention is also characterized by a measuring system which can optically discriminate between the light emission coming from single molecules and the light emission coming from the surrounding solution or impurities. This selectivity is also based on a very dilute reaction solution, so that only one molecule at a time fits in the focal area of the confocal photon-detector, and the background signal emitted by free labelled reagents is minimal. When two-photon excitation is used, the efficiency of the excitation is directly proportional to the square of the efficiency of the excited light. Characteristics of two-photon excitation is that it fundamentally improves the discrimination of scattered light emission from the medium and optical components. The separation methods described above include correlation calculation which makes an essential improvement to the separation. A great advantage of this invention is that there is no longer any need to separate free and bound fractions, either chemically or physically, because an adequate selectivity of free and bound probes can be achieved by a separation method based on optical discrimination and correlation calculations. If necessary, selectivity can be improved with any other known separation method such as washing, filtering and centrifugation.

Fluid handling can be done by means of traditional methods; that is, by dispensing a sample and reagents into a cuvette in which a biospecific reaction occurs in the reaction solution. Fluid handling can also be done in a closed system of flow channels connected to a molecule counter.

This invention's method and the necessary equipment can be realized in many different ways. However, it is essential for this invention that single molecular complexes, which are formed as a result of the reaction and contain at least two fluorescent labels one of which is used to recognize the analyte, are detected fluorometrically by means of molecule counting. The number of detected molecules is directly proportional to the concentration of the analyte $M_k$ to be measured. For the specialist in the field, it is obvious that different applications of this invention may vary within the scope of the claims presented below.

What is claimed is:

1. A biospecific multiparameter assay method for simultaneous measurement of one or several analytes $M_k (k \geq 1)$ in the same reaction solution, said method comprising the steps of:

allowing each sample analyte molecule $M_k$ to react with at least two biospecific probes Ab(j) (j=1,2) labelled with fluorescent labels, to give complex $Ab(k,1)+M_k+Ab(k,2)$;

stopping the reaction by adding a diluent;

focusing a laser beam and photon detectors tuned to the excitation and emission wavelengths, respectively, on the diluted solution; and registering the fluorescent signals and their time domains in the form of single photons from single analyte molecules moving through the focal point, characterized in that the first biospecific probe is labelled with a combination of fluorescent labels $D_k$ ($K_K \leqq 1$), and the second probe is labelled with a fluorescent label F, all labels having different detectable signals and the signals from the complexes $Ab^{D_k}(k,1)+M_k+AB^F(k,2)$ are separated from the background signals and from the signals of other molecules by applying auto-correlation in the time domain and cross-correlation with regard to signals obtained from different labels, and the correlated signals are classified according to $D_k$ in order to determine the number of analyte molecules $M_k$ and their concentration in the sample, and that the excitation of the labels $D_k$ and F is performed by two-photon excitation.

2. The method according to claim 1 characterized in that the fluorescent label F and $D_k$ are composed of fluorescent molecular clusters.

3. The method according to claim 1 characterized by the use of a coincidence circuit controlled by the pulsed laser which is used for background discrimination of signals caused by thermal noise of the photodetector.

4. A counting method for single fluorescent molecules or their complexes which molecules or complexes optionally comprise fluorescent labels F and D, the counting method comprising the steps of:

focusing a laser beam and a photon detector to a diffraction limited volume containing a molecule reacted with two biospecific probes labelled with fluorescent labels; and registering single photon signals and their time domains from single molecules moving through a focal volume, characterized in that the excitation of the fluorescence of the molecules or their complexes is performed by two-photon excitation and the signals from the fluorescence are separated from background signals by means of auto-correlation in the time domain.

5. The method according to claim 4 characterized in that the fluorescent label F and $D_k$ are composed of fluorescent molecule clusters.

6. The method according to claim 4 characterized by the use of a coincidence circuit controlled by the pulsed laser is used for background discrimination of signals caused by thermal noise of the photodetector.

\* \* \* \* \*

UNITED STATES PATENT AND TRADEMARK OFFICE
CERTIFICATE OF CORRECTION

PATENT NO. : 6,204,068 B1
DATED : March 20, 2001
INVENTOR(S) : Erkki Soini and Pekka Hanninen It is certified that error appears in the above-identified patent and that said Letters Patent is hereby corrected as shown below:

Column 15, claim 1,
Line 6, change "$K_K \leq 1$" to -- $k \geq 1$ --.

Column 16, claim 4,
Line 3, change "D" to -- $D_k$ --.

Signed and Sealed this

Eighteenth Day of December, 2001

Attest:

*Attesting Officer*

JAMES E. ROGAN
*Director of the United States Patent and Trademark Office*